US00PP26489P2

(12) United States Plant Patent
Heuger

(10) Patent No.: US PP26,489 P2
(45) Date of Patent: Mar. 8, 2016

(54) *HELLEBORUS* PLANT NAMED 'COSEH 3030'

(50) Latin Name: *Helleborus niger*
Varietal Denomination: COSEH 3030

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 184 days.

(21) Appl. No.: 13/999,074

(22) Filed: Jan. 10, 2014

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 3030', characterized by its upright and mounding plant habit; uniform and freely flowering habit; dark green-colored leaves; freely and early flowering habit; single white to light pink-colored flowers; and good garden performance.

2 Drawing Sheets

Botanical designation: *Helleborus niger.*
Cultivar denomination: 'COSEH 3030'.

BACKGROUND OF THE INVENTION

The present invention relates to a new and distinct cultivar of *Helleborus* plant, botanically known as *Helleborus niger* and hereinafter referred to by the name 'COSEH 3030'.

The new *Helleborus* plant is a product of a planned breeding program conducted by the Inventor in Glandorf, Germany. The objective of the breeding program was to create new uniform *Helleborus* plants with unique and attractive leaf and flower forms and coloration and resistance to pests common to *Helleborus* plants.

The new *Helleborus* plant originated from a cross-pollination conducted by the Inventor in Glandorf, Germany in November, 2007 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in November, 2009.

Asexual reproduction of the new *Helleborus* plant by divisions in a controlled environment in Glandorf, Germany since February, 2010 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3030'. These characteristics in combination distinguish 'COSEH 3030' as a new and distinct *Helleborus* plant:

1. Upright and mounding plant habit.
2. Uniform and freely flowering habit.

3. Dark green-colored leaves.
4. Freely and early flowering habit.
5. Single white to light pink-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger* 'HGC Josef Lemper', disclosed in U.S. Plant Pat. No. 15,615. In side-by-side comparisons conducted in Glandorf, Germany, plants of the new *Helleborus* differed primarily from plants of 'HGC Josef Lemper' in the following characteristics:

1. Plants of the new *Helleborus* had smaller flowers than plants of 'HGC Josef Lemper'.
2. Plants of the new *Helleborus* flowered earlier than plants of 'HGC Josef Lemper'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 3030' grown in a container.

The photograph on the second sheet is a close-up view of a typical opening flower of 'COSEH 3030'.

Red purple-colored spots on the flowers in the photographs are the result of a fungicidal spray application and not a characteristic of the new *Helleborus* plant.

DETAILED BOTANICAL DESCRIPTION

The aforementioned photographs and following observations, measurements and values describe plants grown during the autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger* 'COSEH 3030'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; low vigor to moderately vigorous growth habit.

*Plant height, soil level to top of foliar plane*.—About 14.1 cm.

*Plant height, soil level to top of flowers*.—About 18.1 cm.

*Plant diameter* (*area of spread*).—About 24.9 cm.

Leaf description:

*Arrangement*.—Leaves arranged in a basal rosette; leaves palmately compound with seven leaflets per leaf.

*Leaf length*.—About 11.4 cm.

*Leaf width*.—About 13.5 cm.

*Leaflet length*.—About 7.1 cm.

*Leaflet width*.—About 2.9 cm.

*Leaf shape*.—Palmate; orbicular to reniform in outline.

*Leaflet shape*.—Obovate to narrowly obovate.

*Leaflet apex*.—Obtuse to bluntly acute.

*Leaflet base*.—Attenuate.

*Leaflet margin*.—Serrate.

*Leaflet texture, upper and lower surfaces*.—Smooth, glabrous; leathery.

*Leaflet luster, upper surface*.—Moderately glossy.

*Leaflet luster, lower surface*.—Slightly glossy.

*Leaflet venation pattern*.—Pinnate.

*Leaflet color*.—Developing leaves, upper surface: Between 137B and 138A. Developing leaves, lower surface: Close to 147C. Fully developed leaves, upper surface: Between N137A and 147A; venation, close to 143A to 143B. Fully developed leaves, lower surface: Close to 137B; venation, close to 144C.

*Petioles*.—Length: About 10 cm. Diameter: About 5 mm. Texture, upper and lower surfaces: Smooth, glabrous. Color, upper and lower surfaces: Close to 144B heavily speckled with close to N186C; towards the base, speckling closer to 187C to 187D.

Flower description:

*Flower shape and habit*.—Single rotate flowers typically arranged singly and rarely in pairs; freely and uniform flowering habit with about 33 flowers developing per plant; flowers facing mostly outwardly to slightly nodding.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Flower buds*.—Length: About 2.3 cm. Diameter: About 1.3 cm. Shape: Ovate to elliptic. Color: Close to NN155A.

*Flower diameter*.—About 7.6 cm.

*Flower depth* (*height*).—About 2 cm.

*Petals*.—Transformed into nectaries.

*Sepals*.—Quantity and arrangement: Five, arranged in a single whorl. Length: About 3.6 cm. Width: About 3.4 cm. Shape: Broadly ovate to nearly orbicular. Apex: Obtuse. Base: Broadly cuneate. Margin: Entire. Texture, upper and lower surfaces: Smooth, glabrous. Color: When opening, upper surface: Close to NN155C slightly tinged with close to 186D. When opening, lower surface: Close to NN155C slightly tinged with close to 186C to 186D. Fully opened, upper and lower surfaces: Close to 186C and 186D.

*Peduncles*.—Length: About 12 cm. Diameter: About 4 mm. Aspect: About 35° from vertical. Strength: Moderately strong. Texture: Smooth, glabrous. Color: Close to 150D heavily speckled with close to 187A.

*Reproductive organs*.—Stamens: Quantity per flower: About 120. Filament length: About 1.3 cm. Filament color: Close to NN155D. Anther shape: Reniform; basifixed. Anther length: About 2 mm. Anther color: Close to 3C. Pollen amount: Moderate. Pollen color: Close to 4C to 4D. Pistils: Quantity per flower: About five to seven. Pistil length: About 7 mm. Stigma shape: Club-shaped. Stigma color: Close to 155A. Style length: About 6 mm. Style color: Close to 186D. Ovary color: Close to 150D. Nectaries (transformed petals): Quantity per flower: About 15. Length: About 8 mm. Diameter: About 2.5 mm. Shape: Tubular, flattened. Color, immature, inner and outer surfaces: Close to 154C; towards the base, close to 145A. Color, mature, inner and outer surfaces: Close to 3C; towards the base, close to 145A.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 3030' as illustrated and described.

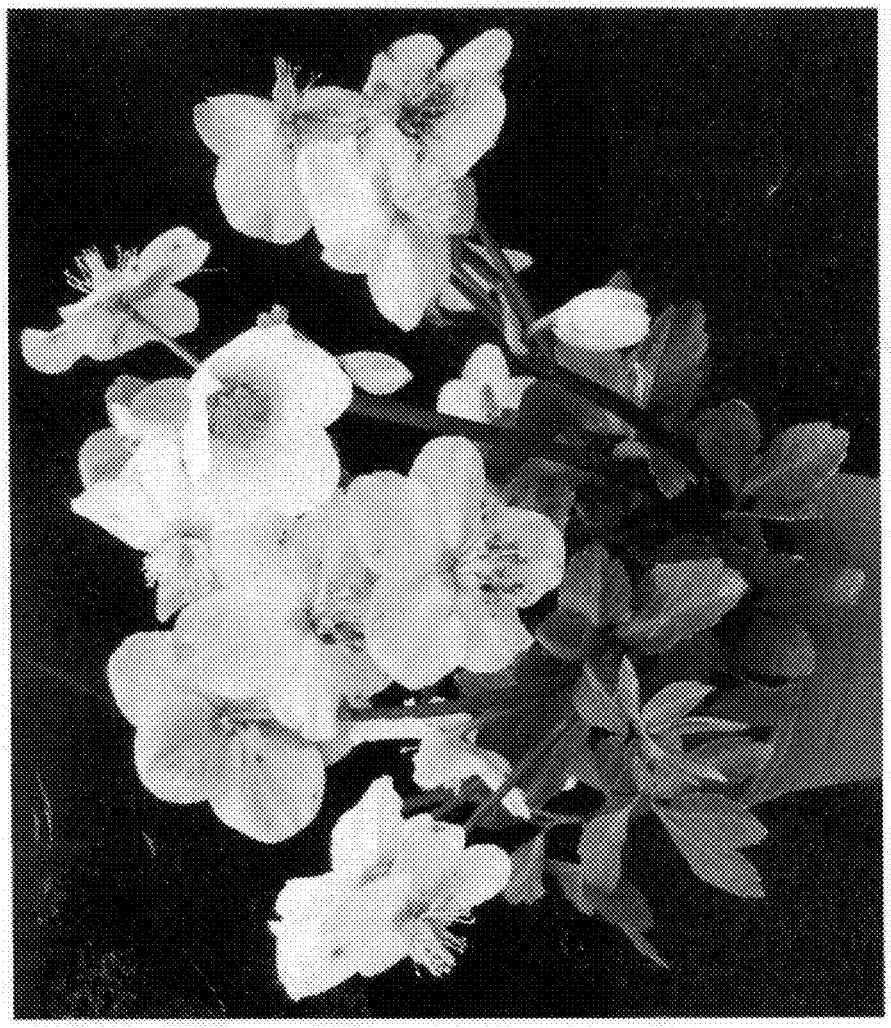

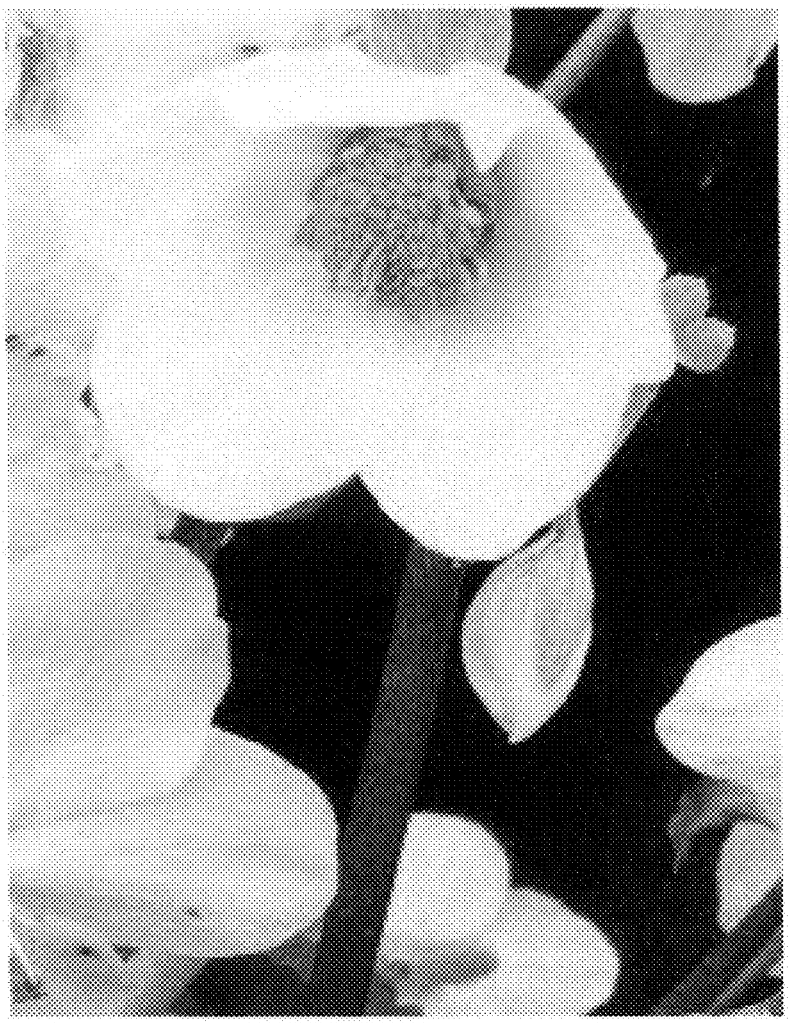

* * * * *